(12) United States Patent
Heumann

(10) Patent No.: US 6,765,981 B2
(45) Date of Patent: Jul. 20, 2004

(54) COMPUTED TOMOGRAPHY

(75) Inventor: John M Heumann, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 174 days.

(21) Appl. No.: 10/209,378

(22) Filed: Jul. 31, 2002

(65) Prior Publication Data

US 2004/0022348 A1 Feb. 5, 2004

(51) Int. Cl.$^7$ ............................................. G01N 23/083
(52) U.S. Cl. ............................ 378/4; 378/8; 378/901
(58) Field of Search ............................ 378/4, 8, 15, 19, 378/901

(56) References Cited

U.S. PATENT DOCUMENTS

| | | | |
|---|---|---|---|
| 4,305,127 A | * 12/1981 | Heuscher | 600/425 |
| 5,640,436 A | * 6/1997 | Kawai et al. | 378/4 |
| 6,002,739 A | 12/1999 | Heumann | |
| 6,242,743 B1 | * 6/2001 | DeVito et al. | 250/363.05 |
| 6,490,334 B1 | * 12/2002 | Wang et al. | 378/15 |
| 6,618,467 B1 | * 9/2003 | Ruchala et al. | 378/65 |

FOREIGN PATENT DOCUMENTS

WO    WO 2058009 A1 * 7/2002 ........... G06T/11/00

OTHER PUBLICATIONS

A. C. Kak and Malcolm Slaney, "Principles of Computerized Tomographic Imaging," 1988, 276–285.

Y. Censor, "Finite Series–Expansion Reconstruction Methods," 1983, Proc. IEEE 71:409–419.

H. Robbins and S. Monro, "A Stochastic Approximation Method," 1951, Annals of Mathematical Statistics, 22:400–407.

* cited by examiner

*Primary Examiner*—David V Bruce

(57) ABSTRACT

A system and method of computed tomography is disclosed. The method includes acquiring at least one projection but less than all projections to be used in reconstruction of an unknown object and processing the at least one projection for reconstruction of the unknown object. After processing each projection is discarded. Projections are acquired until all projections have been processed. An estimate of the unknown object may be generated during the processing of each of the projections.

20 Claims, 3 Drawing Sheets

COMPUTED TOMOGRAPHY

BACKGROUND

Tomography, as used here, is a general term describing various techniques for imaging one or more cross-sectional "focal plane(s)" through an object. Since contiguous focal planes can describe a volumetric region, this definition also encompasses reconstruction of arbitrary volumes. Tomography typically involves forming projections of a region of interest using some type of penetrating radiation, e.g. x-rays, sound waves, particle beams, or products of radioactive decay, combined with application of a reconstruction technique. Tomography has been applied in diverse fields to objects ranging in size from microscopic to astronomical. X-ray tomography, for example, is commonly used to inspect solder joints for defects formed during fabrication of printed circuit assemblies.

Computed tomography (CT) is a computational technique for reconstruction of cross-sectional images formed by processes which can be described (or approximated) by line integrals. To see that x-ray absorption imaging falls into this category, note that the relative attenuation of a monochromatic beam of x-radiation as it passes through an absorbing material is given in the non-diffracting case by the following equation:

$$\frac{I}{I_0} = e^{-\oint \sigma(r)dr}$$

Where:

$$\frac{I}{I_0}$$

is the relative attenuation of the monochromatic beam of x-radiation, σ is the linear absorption coefficient, and the integral is to be evaluated along the beam path r. Taking the natural log of both sides results in the following form:

$$-\ln\left(\frac{I}{I_0}\right) = \oint \sigma(r)dr$$

A discrete approximation to this line integral is typically used in practice, as follows:

$$y_i = \ln\left(\frac{I}{I_0}\right)_i = \sum a_{ij}x_j$$

Where: $y_i$ is a measured projection, $a_{ij}$ is the path length of the intersection between ray i and voxel (a three-dimensional pixel) j, and $x_j$ reflects the effective linear absorption coefficient within that voxel.

Methods for CT reconstruction have been widely discussed in the literature and will be summarized only briefly here. Transform methods rely on discrete approximations to inversion of the Radon transform in one form or another. Often, the Fourier slice theorem is exploited. The Fourier slice theorem states that the Fourier transform of a parallel projection of an object gives a slice through the Fourier transform of the object. In direct inversion, the Fourier transforms of the projections are used to build up an estimate of the Fourier transform of the object, which is then interpolated and inverted. In filtered backprojection, the Fourier transforms of the projections are multiplied by an appropriate filter function, and then the resulting values projected back along the paths of the incoming rays (hence, the term backprojection). Although derived from identical starting points, the two approaches have different computational requirements and different behavior in practical implementations. Filtered backprojection is typically favored in most implementations today, although there is continued research interest in direct inversion.

In contrast to transform methods, which derive from the inverse Radon transform, series-expansion methods for tomographic reconstruction, also known as algebraic reconstruction methods, directly seek a solution to the discrete ray equations y=Ax, where A is a matrix and x is a single row matrix. Noise-limited projection data frequently result in an underdetermined and inconsistent set of equations, so approximate solutions must be sought. Additionally, the system of equations is typically too large for inversion or singular value decomposition to be attractive. Instead, iterative methods related to Kaczmarz's "method of projections" are used, which are described in A. C. Kak and Malcolm Slaney, "Principles of Computerized Tomographic Imaging," IEEE Press, 1988, 276–285 and incorporated by reference herein. Among the better known are Algebraic Reconstruction Techniques (ART) including several variants, such as additive and multiplicative ART, Simultaneous Iterative Reconstructive Technique (SIRT), and Simultaneous Algebraic Reconstruction Technique (SART), which are described in Y. Censor, 1983, "Finite Series-Expansion Reconstruction Methods." Proc. IEEE 71:409–419 and incorporated by reference herein. The various methods differ in the criteria used to choose a solution, the updating rule they use, and in the manner in which they sequence over the available projection data.

Many implementations of CT treat a 3-dimensional object as made up of adjacent, 2-dimensional slices (as in computerized axial tomography or CAT scanning) and compute multiple 2-D tomographic reconstructions. Direct 3D reconstructions are also done, generally on the basis of Grangeat's method or variations thereof.

Computed tomography has the potential for more accurate reconstructions than laminography or tomosynthesis. Indeed, using complete data (projections from all angles), CT can be shown to provide an optimal, band-limited approximation to an object of finite size. If the original object is itself discrete, CT reconstruction can often be shown to be an exact model of the object. Shadowing artifacts and loss of high-frequency components are dramatically reduced, compared to laminography or tomosynthesis. Highly accurate reconstructions come with a price, however. CT typically requires many projections and is computationally intensive. As a result, its use to date has largely been limited to areas (such as medicine) where multi-million dollar machines can be economically justified.

As described above, current CT technology is not optimal for many tasks, including the inspection of printed circuit boards. Modem circuit boards are generally double-sided and utilize mainly surface-mount technology (SMT) parts in a variety of package styles. Additionally, through-hole components or pin-grid-array (PGA) parts may be used in some instances. Visual inspection or automated optical inspection (AOI) are inadequate for these boards, since many SMT joints are hidden under the component body. Since components are mounted on both sides of the board, simple transmission radiography is also not adequate, and some form of cross-sectional imaging is required.

Additionally, for some solder joint types, multiple slices at different depths are required for adequate characterization. CT would be ideal in terms of image quality, but is seldom used due to the large number of projections required and the associated costs. True 3-D tomography using cone beam illumination, rather than axial tomography, is desirable for efficient use of x-ray photons, and because projections in the plane of the board are typically impractical due to the excessive absorption. Laminography and tomosynthesis are both currently used for PCB inspection, but suffer from poorer image quality than would be available with CT. As noted above, both techniques suffer from shadowing artifacts, since out-of-focus information is blurred but not actually removed from the reconstructed slices.

Present techniques for CT require all of the projection data to be available before reconstruction can begin. In some architectures, this can lead to large storage requirements and delays in processing (i.e., throughput problems). When each projection is a two-dimensional image, for example a 1024× 1024 element image digitized with 12-bit resolution, more than one megabyte of storage is required for each projection. Additionally, in some tomographic systems, collection of projections for the first region of interest may be interleaved with collection of projections for other regions of interest. As a result, the system may be required to store large amounts of projection data before reconstruction can begin.

SUMMARY

A system method for computed tomographic imaging is described. The system and method allows for beginning the processing for the reconstruction with as few as one projection, thus eliminating the requirement that a complete set of projections is available before reconstruction is attempted.

In one embodiment, the method includes acquiring at least one projection but less than all projections to be used in reconstruction of an unknown object and processing the at least one projection for reconstruction of the unknown object. Processing the projection(s) may include revising an estimate of the unknown object.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

Various aspects of the invention will now be described with reference to the following figures ("FIGS.") which are not necessarily drawn to scale, but use the same reference numerals to designate corresponding parts throughout each of the several views.

DETAILED DESCRIPTION

Figure 1:
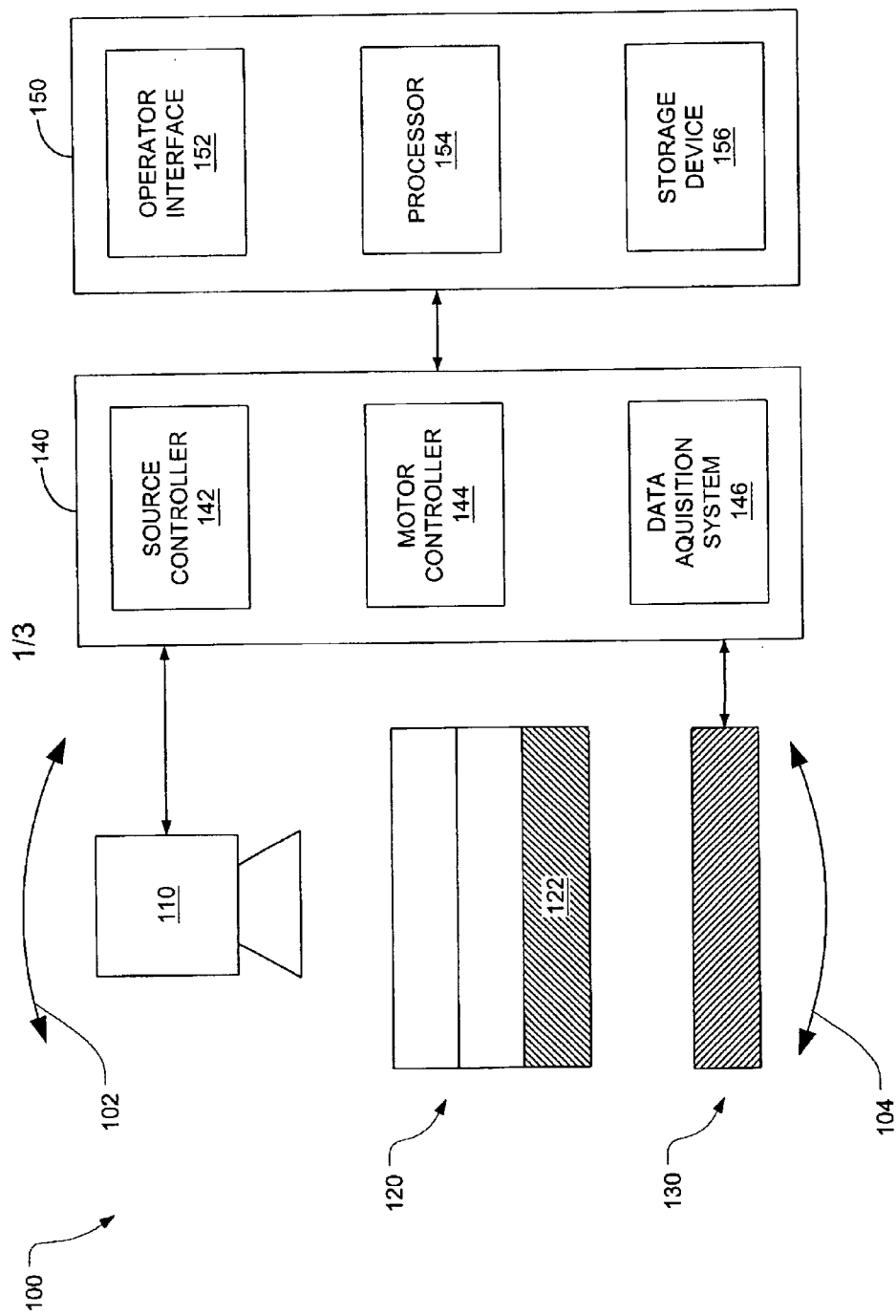
FIG. 1 is a schematic diagram of one embodiment of a tomography system according to the present invention.

A computed tomography reconstruction formulated so that each projection is processed immediately after acquisition and then discarded not only drastically reduces storage requirements, but allows computation to begin as soon as the first projection has been acquired and which could be overlapped with acquisition of subsequent images. This type of "online" or incremental learning is widely practiced in machine learning and statistical pattern recognition, as exemplified by the Robbins-Monro algorithm, which is described in Robbins, H. and S. Monro, 1951, "A stochastic approximation method," Annals of Mathematical Statistics, 22:400–407 and is incorporated by reference herein, and the online version of backpropagation for training neural networks. An online reconstruction of tomographic images can also be achieved using an approach based on or similar to the Robbins-Monro algorithm.

Briefly, the Robbins-Monro algorithm and its variants provide a method for finding a root or extremum of a stochastic function in which the estimates of the function parameters are revised as each data point is presented. This is in contrast to typical regression approaches, which require storage of all measured data points before computation can begin.

One particular well known Robbins-Monro application is the training of feedforward neural networks by backpropagation. If all of the training data is stored, backpropagation of errors provides the gradient of the objective function with respect to the weights. This is typically termed batch or offline learning. Conversely, if the contribution to the gradient is computed after each sample and the weights adjusted accordingly, online training, in which a stochastic approximation to the gradient is used rather than the actual gradient, is achieved. This not only reduces storage requirements and allows computation to begin as soon as the first sample is available, but also can help avoid the local minima due to the stochastic nature of the approximation to the gradient.

The Robbins-Monro algorithm also provides a prescription for how to adjust step size so as to guarantee convergence in the limit of unlimited data. Essentially, step size is chosen so that the variance remains finite while the change in weights can be infinite.

In the series formulation of computed tomography, each projection leads, after linearization, to an equation of the form, $y_i = A_i x$, where i is the projection number, $y_i$ is the measured projection, x is the unknown object being solved for, and $A_i$ is a known matrix determined by the geometry and other properties of the imaging system.

Equations for the individual projections can be combined leading to a system of equations, $y = Ax$. This system of equations is typically inconsistent, and may be over- or under-determined, depending on the number of projections and the voxellation. Series methods, like Algebraic Reconstruction Technique (ART), Simultaneous Iterative Reconstructive Technique (SIRT), Simultaneous Algebraic Reconstruction Technique (SART), Maximum Entropy (MENT), etc., provide iterative solutions to this system of equations, without attempting to directly invert the system matrix which, while sparse, is typically large and singular. In essence, A is used to compute (simulate) the projection data that would be expected, given the current estimate of x. The error between the computed and measured projection data is then used to revise the estimate of x. The methods differ in the particular update rule used, and in whether corrections are applied ray-by-ray, or accumulated over all rays before application. A typical additive ART updating rule, for example, as follows:

$$^{k+1}x = {^k}x + \lambda_k \frac{y_i - (a_i \cdot {^k}x)}{a_i \cdot a_i} a_i$$

Where: $\lambda_k$ is a step size for iteration k, and $a_i$ is the $i^{th}$ row of matrix A. This rule would typically be applied ray-by-ray, cycling through all rays of all projections at each iteration. SIRT updates are similar, except that correction terms are accumulated from all rays of all projections prior to altering x.

One way to modify ART, SIRT, or the other series methods to online reconstruction is to apply the update rule after each individual projection, while choosing step sizes to satisfy the Robbins-Monro convergence theorem.

FIG. 1 is a schematic diagram of one embodiment of a tomography system 100 according to the present invention. The term "tomography" is used here to include both static and dynamic tomography. The tomography system 100 includes at least one source 110, an object 120, a detector 130, a control mechanism 140, and a computer 150. The arrows 102 and 104 illustrate that the source 110 and/or the detector 130 are repositioned between each projection (for static tomography) or moved during image acquisition (for dynamic tomography). Alternatively, or in addition, the object 120 may also be moved during or between multiple acquisition cycles. Hybrid systems, in which motion occurs both between and during image acquisition, are also possible.

The source 110 may be any conventional x-ray, or other suitable penetrating energy, source for passing energy through the object 120 to the detector 130. The illustrated object 120 includes at least one surface or volume 122 that is under investigation as the desired focal region in FIG. 1. For example, the surface of interest 122 may be one side of a printed circuit board assembly having solder connections that are to be non-destructively inspected. The surface of interest 122, for which a cross-sectional image is desired, may also lie partly or entirely in the interior of object 120. The detector 130 shown in FIG. 1 senses and/or records energy from the source 110 which has passed through the object 120.

The control mechanism 140 includes a source controller 142 that provides power and timing signals to source 110, a motor controller 144 that controls the rotational speed and position of source 110 and detector 130, and a data acquisition system 146 that acquires data from detector 130 and passes the data to the computer 150.

The computer 150 includes an operator interface 152, a processor 154, and a storage device 156. An operator provides commands and scanning parameters to the processor 154 via the operator interface 152. The processor 154 uses the operator provided commands and parameters to provide control signals and information to the source controller 142, the motor controller 144, and the data acquisition system 146. Data received by the data acquisition system 146 is stored in the storage device 156. The processor 154 accesses the data in the storage device 156 and performs image reconstruction. The reconstructed image is stored in the storage device 156. The storage device 156 may include one or more storage devices.

Figure 2:
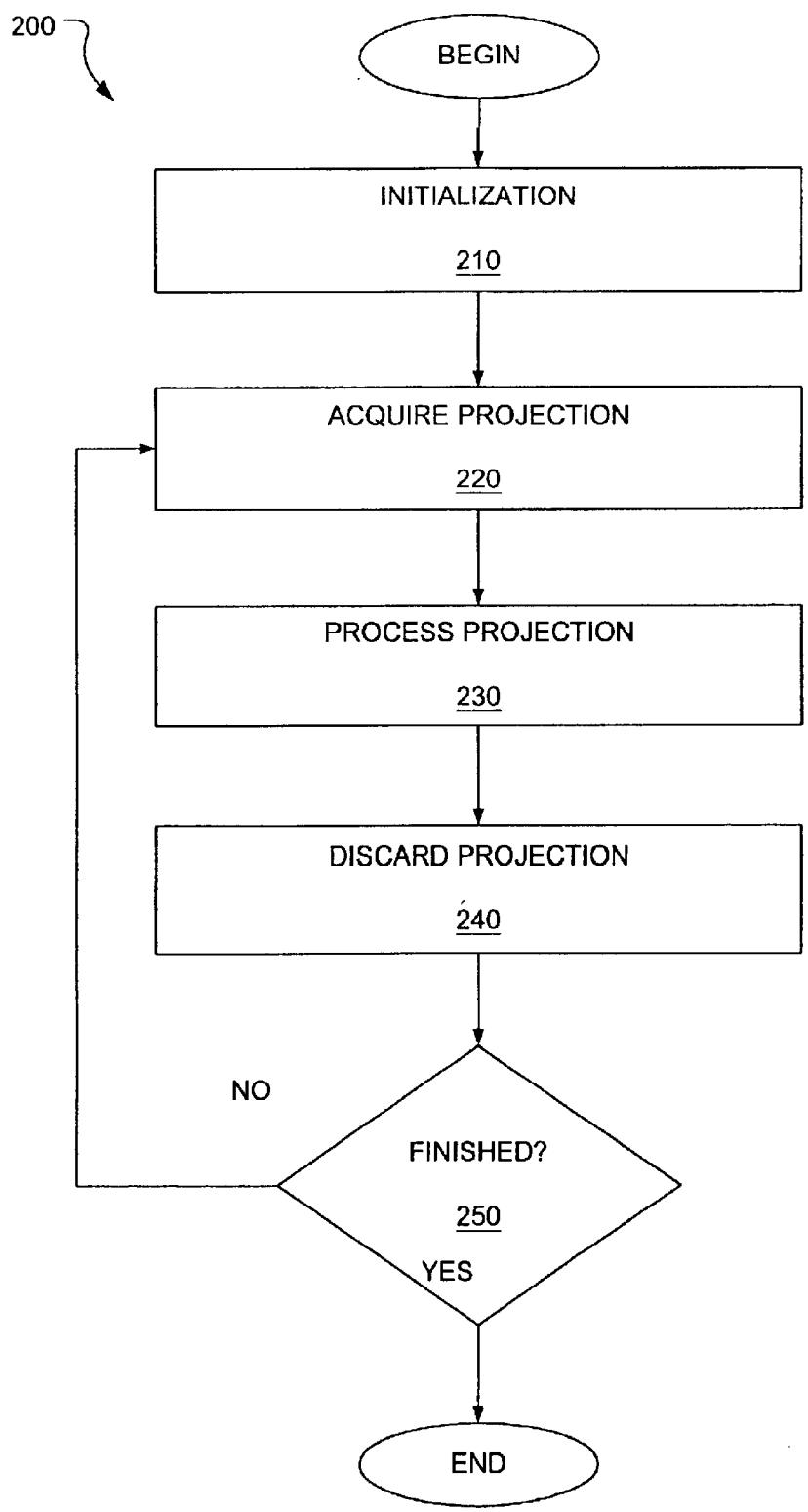
FIG. 2 is a flowchart for an embodiment of computed tomography method.
Figure 3:
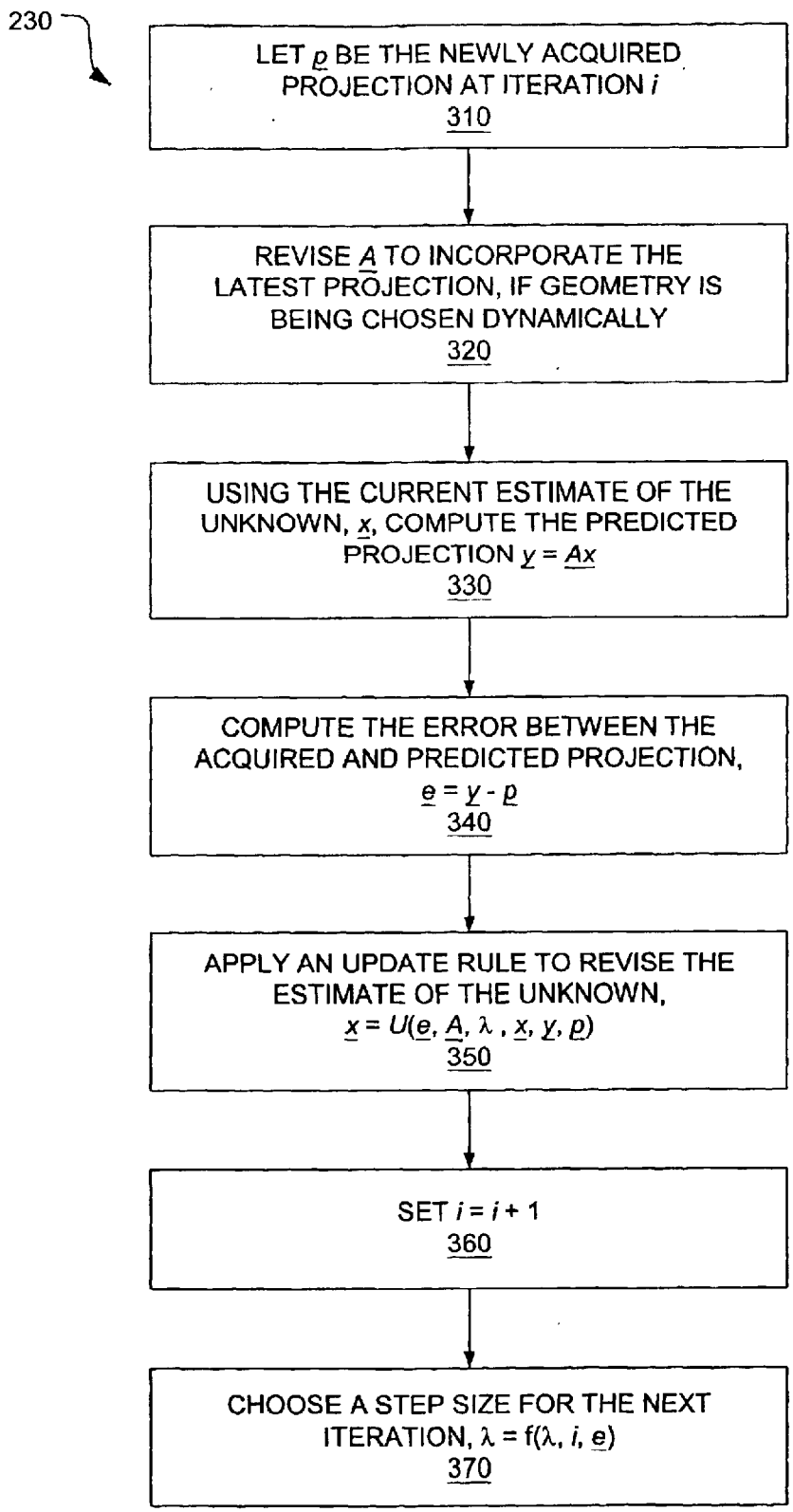
FIG. 3 is a flowchart showing one of the steps in FIG. 2 in more detail.

FIGS. 2 and 3 show the architecture, functionality, and operation of a tomography method 200 that may be implemented with the tomography system shown in FIG. 1 and/or other tomography systems.

Each block in FIGS. 2 and 3 represents an activity, step, module, segment, or portion of computer code that will typically comprise one or more executable instructions for implementing the specified logical function(s). However, a variety of other of computer, electrical, electronic, mechanical, and/or manual systems may also be similarly configured to operate in a similar manner. It should also be noted that, in various alternative implementations, the functions noted in the blocks will occur in an order different than noted in figures. For example, multiple functions in different blocks may be executed substantially concurrently, in a different order, incompletely, and/or over an extended period of time, depending upon the functionality involved. Various steps may also be completed manually.

The tomography method 200 begins with an initialization at step 210. The initialization step includes setting the initial step size and estimate of x (often just a constant value, although it may be more complex if prior information is available), as well as computing matrix A, if the geometry is known in advance. Step 220 includes the acquisition of a projection view. At step 230, the acquired projection is processed. After the projection has been processed, the projection is discarded as shown in step 240. At step 250, a test for completion is made. If reconstruction is not yet complete, the process returns to step 220. The test for completion can be made in a variety of ways. For example, termination may occur after a specific number of projections are processed or when an accumulated error function converges to be below a specified threshold. Both the number of projections and the geometry can be specified in advance, as is typical, or chosen dynamically at runtime. In the latter case, parts of A would have to be computed dynamically during reconstruction. Processing of individual projections described above may occur in parallel, may be interleaved, or may be overlapped with acquisition of other projections.

Various aspects of step 230 are shown in more detail in FIG. 3. At step 310, p is the newly acquired projection (in the format of y) at iteration i. If the projection geometry is being chosen dynamically, revise A to incorporate the latest projection in step 320. (If, as is more typical, the projection geometry is fixed in advance, A will have already been computed in the initialization step 210 of FIG. 2). At step 330 given the current estimate of the unknown, x, compute the projection that would have been predicted by y=Ax. Compute, in step 340, the error between the acquired and predicted projection, e=y−p. At step 350, apply an update rule to revise the estimate of the unknown, x=U(e A, $\lambda$, x, y, p), e.g. the SIRT update described previously. At step 360, increment the iteration by setting i=i+1. At step 370, choose a step size for the next iteration $\lambda$=f($\lambda$, i, e). A simple step size update that has been used successfully is $\lambda$=1.0/(1.0+i/2.0).

With some geometries it is advantageous to process projections in groups, rather than singly. For example, with a circular, planar geometry like that used in the Agilent Technologies 5DX laminography system, it is found to be advantageous to group pairs of projections which are ~180° apart, and process them together as a single iteration. As an additional example, if projections were taken with the source positioned at the vertices of m nested n-gons, it might be desirable to process the projections from all the vertices of a particular polygon together . . . i.e. to use a group size of n.

As noted above the tomography method 200 shown in FIGS. 2 and 3 may be implemented in a wide variety of electrical, electronic, computer, mechanical, manual, and/or other configurations. However, in a typical embodiment, the method 200 will be at least partially computerized with various aspects of the system being implemented by software, firmware, hardware, or a combination thereof.

When the tomography method 200 is at least partially implemented in hardware, the system may be implemented using a variety of technologies including, but not limited to, discrete logic circuit(s) having logic gates for implementing logic functions upon data signals, application specific integrated circuit(s), "ASIC(s)", having appropriate combinational logic gates, programmable gate array(s), "PGAs", and/or field programmable gate array(s), "FPGAs. When implemented in software, the tomography method 200 may be part of a source program (or "source code"), executable program ("object code"), script, or any other entity comprising a set of instructions to be performed as described in more detail below. Such software may be written using an object oriented programming language having classes of data and methods, and/or a procedure programming language, having routines, subroutines, and/or functions. For example, suitable programming languages include, but are not limited to, C, C++, Pascal, Basic, Fortran, Cobol, Perl, Java, and Ada.

Such software may be stored on any computer readable medium for use by, or in connection with, any computer-related system or method. For example, the computer readable medium may include any electronic, magnetic, optical, or other physical device or means that can contain or store a computer program for use by, or in connection with, a computer-related system or method. The computer-related system may be any instruction execution system, apparatus, or device, such as a computer-based system, processor-containing system, or other system that can fetch the instructions from the instruction execution system, apparatus, or device and then execute those instructions. Computer-readable medium therefore includes any means that will store, communicate, propagate, or transport the program for use by, or in connection with, the instruction execution system, apparatus, or device.

For example, the computer readable medium may take a variety of forms including, but is not limited to, an electronic, magnetic, optical, electromagnetic, infrared, or semiconductor system, apparatus, device, or propagation medium. More specific examples of a computer-readable medium include, but are not limited to, an electrical connection (electronic) having one or more wires, a portable computer diskette (magnetic), a random access memory ("RAM") (electronic), a read-only memory ("ROM") (electronic), an erasable programmable read-only memory ("EPROM," "EEPROM," or Flash memory) (electronic), an optical fiber (optical), and a portable compact disc read-only memory ("CDROM") (optical). The computer readable medium could even be paper or another suitable medium upon which the program is printed, as the program can be electronically captured, for instance via optical sensing or scanning of the paper, and then compiled, interpreted or otherwise processed in a suitable manner before being stored in a memory.

In a typical embodiment, once the hardware and/or software implementation of the tomography system shown in FIG. 1 is accessed, a processor will typically be configured to execute instructions corresponding to the method 200 in conjunction with an operating system stored within a memory. The processor will also receive and execute further instructions and data stored in memory or made available from various input/output devices (such as the source and/or detector assemblies discussed above) so as to generally operate the system pursuant to the instructions and data contained in the software and/or hardware.

Combining the above described method with the Multi-lminar Tomography approach described in U.S. Pat. No. 6,002,739, which is incorporated by reference herein, results in a computed tomographic reconstruction technique which is fast, has minimal storage requirements, is amenable to parallel processing, performs well with limited projection data, and can readily incorporate prior constraints on the reconstruction solution.

It should be emphasized that the embodiments described above, and particularly any "preferred" embodiments, are merely examples of various implementations that have been set forth here to provide a clear understanding of various aspects of the invention. One of ordinary skill will be able to alter many of these embodiments without substantially departing from scope of protection defined solely by the proper construction of the following claims.

What is claimed is:

1. A method of computed tomography of an unknown object comprising:
   acquiring at least one projection, but less than all projections to be used in reconstruction of the unknown object; and
   revising an estimate of the unknown object using the at least one projection to obtain a new estimate.

2. The method of claim 1, further comprising:
   acquiring another at least one projection; and
   revising the new estimate of the unknown object using the another at least one projection.

3. The method of claim 1, farther comprising acquiring another at least one projection concurrently with revising the estimate of the unknown object.

4. The method of claim 1, wherein revising an estimate includes:
   calculating a predicted projection using the estimate of the unknown object;
   calculating an error between the acquired projection and the predicted projection; and
   applying an update rule to revise the current estimate of the unknown object using the calculated error to obtain the new estimate.

5. The method of claim 1, wherein revising an estimate includes choosing a step size for selection of a subsequent projection.

6. The method of claim 1 further comprising acquiring another at least one projection concurrently with acquiring the at least one projection, and revising the estimate of the unknown object using the another at least one projection to obtain another new estimate concurrently with revising the estimate of the unknown object using the at least one projection to obtain the new estimate.

7. The method of claim 1 further comprising setting an initial estimate of the unknown object.

8. The method of claim 1, wherein revising an estimate includes using a series reconstruction method.

9. The method of claim 1, further comprising discarding the at least one projection.

10. The method of claim 1, wherein acquiring at least one projection includes acquiring a pair of projections separated by approximately 180 degrees.

11. A method of computed tomography of an unknown object comprising:
    acquiring at least one projection, but less than all projections to be used in reconstruction of the unknown object; and
    processing the at least one projection for reconstruction of the unknown object.

12. The method of claim 11, further comprising:
    acquiring another at least one projection; and processing the another at least one projection for reconstruction of the unknown object.

13. The method of claim 11, further comprising acquiring another at least one projection concurrently with processing the at least one projection for reconstruction of the unknown object.

14. The method of claim 11, wherein processing each projection includes:
    calculating a predicted projection using an estimate of the unknown object;
    calculating an error between the acquired projection and the predicted projection; and
    applying an update rule to revise the estimate of the unknown object using the calculated error to obtain a new estimate.

15. The method of claim 11, wherein processing the at least one projection includes setting a step size for selection of a subsequent projection.

16. The method of claim 11 further comprising acquiring another at least one projection concurrently with acquiring the at least one projection, and processing the another at least one projection for reconstruction of the unknown object concurrently with processing the at least one projection for reconstruction of the unknown object.

17. The method of claim 11 further comprising setting an initial estimate of the unknown object.

18. The method of claim 11, wherein processing each projection includes using a series reconstruction method.

19. The method of claim 11, wherein acquiring at least one projection includes acquiring two projections separated by approximately 180 degrees.

20. A computed tomography system comprising:
    means for acquiring at least one projection, but less than all projections to be used in reconstruction of an unknown object; and
    means for processing the at least one projection for reconstruction of the unknown object.

* * * * *